(12) United States Patent
Hageman

(10) Patent No.: US 6,544,547 B2
(45) Date of Patent: *Apr. 8, 2003

(54) NUTRITIONAL COMPOSITION CONTAINING METHIONINE

(75) Inventor: Robert Johan Joseph Hageman, Waddinxveen (NL)

(73) Assignee: N. V. Nutricia, Zoetermeer (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,757

(22) PCT Filed: Jul. 14, 1998

(86) PCT No.: PCT/NL98/00408

§ 371 (c)(1),
(2), (4) Date: Jan. 31, 2000

(87) PCT Pub. No.: WO99/03365

PCT Pub. Date: Jan. 28, 1999

(65) Prior Publication Data

US 2002/0142025 A1 Oct. 3, 2002

(30) Foreign Application Priority Data

Jul. 14, 1997 (EP) .................................. 97202206

(51) Int. Cl.[7] .......................... A61K 47/00; A61K 9/14; A61K 9/50
(52) U.S. Cl. ...................... 424/439; 424/400; 424/464; 424/489; 424/450; 424/484; 424/499
(58) Field of Search ................. 424/489, 450, 424/400, 439, 464, 484, 499

(56) References Cited

U.S. PATENT DOCUMENTS

| 4,871,550 | A | * | 10/1989 | Millman | .................. 424/601 |
| 5,215,750 | A | | 6/1993 | Keane, II | |
| 5,480,865 | A | * | 1/1996 | Kingham | .................. 514/2 |
| 5,817,329 | A | * | 10/1998 | Gardiner | .................. 424/439 |

FOREIGN PATENT DOCUMENTS

| EP | 0120705 A2 | * | 3/1984 | ............ A23G/3/00 |
| EP | 0120705 A2 | * | 3/1984 | ............ A23G/3/00 |
| EP | 0259167 A2 | | 3/1988 | |
| EP | 0482715 A1 | | 4/1992 | |
| EP | 0532369 A2 | | 3/1993 | |
| GB | 2292522 A | | 2/1996 | |

* cited by examiner

Primary Examiner—Thurman K. Page
Assistant Examiner—Robert M. Joynes
(74) Attorney, Agent, or Firm—Young & Thompson

(57) ABSTRACT

An enteral food composition for clinical or dietary use, comprises, in addition to carbohydrates and proteins or their hydrolysates the following components or their nutritional equivalents, per daily dosage: methionine (0.6–7 g), cysteine (0.5–2.5 g), folic acid (0.4–8 mg), pyridoxal (vitamin $B_6$) (3–20 mg), zinc (18–120 mg) and at least 400 kcal energy in the form of carbohydrates. These amounts are well above the Recommended Daily Allowance (RDA) values. Further preferred components include lecithin, cyanocobalamine, betaine and magnesium, as well as transsulfuration metabolites, ATP enhancers and antioxidants.

10 Claims, No Drawings

NUTRITIONAL COMPOSITION CONTAINING METHIONINE

This application is a 371 of PCT/NL98/00408 filed Jul. 14, 1993.

FIELD OF THE INVENTION

The present invention relates to a module of nutritional components which supports total methionine metabolism in man, for use in a universal medicinal food. The invention also relates to food products containing this module and to a method of producing food products by using selected amounts of the module.

BACKGROUND

Methionine is metabolised in man via a multi-step pathway, the transsulfuration pathway. Several intermediate products are formed in this pathway, which play a dominant role in other biochemical pathways as well. For example, the reaction product S-adenosyl methionine is extensively used in many methylation reactions; homocysteine is the main methyl acceptor in folate metabolism and also the conversion of betaine to dimethylglycine (via methylation of homocysteine) strongly influences folate metabolism.

Another intermediate in the transsulfuration pathway is cystathionine generated by reaction between homocysteine and serine, that may split into cysteine and 2-oxy-butyrate. The latter is involved in the metabolism of several other compounds (e.g. threonine). Cysteine is metabolised to various useful products such as taurine and sulphates. It is also an important precursor for glutathione in the liver and some other tissues. Glutathione that is produced in the liver has to be transported to cell compartments in some peripheral organs in order to exhibit its activity. Intracellular glutathione levels are in turn strongly influenced by the presence of reducing equivalents and amino acids in the cell.

Herein we define total methionine metabolism as those biochemical pathways which occur in mammals and in which metabolites of the methionine transsulfuration pathway (methionine, S-adenosyl methionine, S-adenosyl homocysteine, homocysteine, cystathionine and cysteine) and main metabolites thereof (taurine and glutathione) are involved (see scheme below).

Many diseases in man have been associated with impaired functioning of parts of total methionine metabolism. Lack of the body capacity for methylation (by shortages of available S-adenosyl methionine) has been related to diseases like cancer, improper wound healing, diabetes, neurological diseases like Alzheimer or Parkinson' disease (WO 96/33703). Shortages of folate have been associated with neural defects and several other problems.

Dysfunction of methionine metabolism may also lead to increased homocysteine plasma levels, which are associated with cardiovascular problems. Cysteine deficiencies may lead to low taurine levels, low sulphation capacity and low intracellular glutathione levels. Shortages of cysteine have been associated with diseases like diabetes, cardiovascular disease, cancer, rheumatoid arthritis, etc.

Glutathione can play many important roles in the cell. A substantial part of glutathione must be in the reduced form (having a specific redox potential) in order to allow it to be active. Deficiencies of glutathione have been associated with all kinds of radical-mediated diseases, such as chronic inflammations, rheumatoid arthritis, with the occurrence of cancer and impaired immune functions against infection.

EP-A-532369 (Bissbort) describes the pharmaceutical use of L-methionine for enhancing the methylation capacity in man, e.g. for improving the immune response, combating viral infections and increasing creatine production. Methionine may be combined with folic acid, pyridoxine (vitamin $B_6$), cyanocobalamine (vitamin $B_{12}$) and magnesium. A daily dose comprises 1.5–5 g (3 g) of L-methionine, 250–2500 mg (600 mg) of magnesium chloride, 30–120 mg (100 mg) of magnesium carbonate, 0.6–20 mg (8 mg) of folic acid, 1.5–25 mg (10 mg) of vitamin $B_6$ and 15–25 µg (20 µg) of vitamin $B_{12}$.

WO 93/15738 (Waldthaler) discloses medicaments containing thymine or its equivalents in combination with methionine, pyridoxine and/or cyanocobalamine and optionally penicillin G for the treatment of disorders in the folate metabolism.

WO 96/02252 and WO 96/33727 (Knoll) disclose the use of S-adenosyl-L-methionine for the treatment of damage caused by temporary and permanent local ischaemias, respectively.

EP-A-347864 (Strydom) discloses an anti-atherogenic agent which lowers the plasma level of free sulphydryl groups of homocysteine and cysteine and which can contain oxidising agents and folic acid, pyridoxine (vitamin $B_6$), cyanocobalamine (vitamin $B_{12}$) and choline or betaine.

Likewise, EP-A-595005 and EP-A-595006 (Vesta) teach the use, for adults and infants respectively, of specific ratios of folic acid, pyridoxine and cyanocobalamine for suppressing high homocysteine and methionine levels in plasma, which are the cause of metabolic disturbances. According to the latter document, pyridoxine should at least partly be present in its accessible pyridoxal form. Riboflavin (vitamin $B_2$), ascorbic acid (vitamin C), tocopherol (vitamin E), zinc and selenium may also be present.

EP-A-705542 discloses a complete dietary composition for adolescents and especially for children of 1 to 6 years having diseases such as intestinal disorders. The composition contains 50–65 (63) energy % of carbohydrates, 20–35 (25) en. % of fats and 10–20 (12) en. % of free amino acids with a specific amino acid content.

A multivitamin preparation supporting the immune system is disclosed in GB-A-2,292,522. It contains an amino acid blend, vitamins C, E, A, D and B complex, minerals and trace elements. Important amino acids are: methionine (90 mg), valine, leucine, threonine (70 mg), phenylalanine, lysine, isoleucine and tryptophane. Levels of B complex vitamins may be: B1 (50 mg), B2 (100 mg), B6 (100 mg), pantothenic acid (300 mg), nicotinamide (50 mg), B12 (2.5 µg), folic acid (150 µg) and biotin (50 µg). The preparation does not contain carbohydrates or full proteins. No recommended dosages are given.

U.S. Pat. No. 5,215,750 discloses a composition for inducing weight loss, containing glutamine as the major component, and further a broad range of vitamins and minerals, without further amino acids, proteins, carbohydrates or fats.

Despite these proposals, the diseases referred to above are still very common and therefore there exists a need for nutritional products that may support prevention and treatment of these diseases.

Many persons suffer from deficiencies in essential amino acids, such as methionine, essential fatty acids, vitamins, minerals, trace elements or other food components, as a result of bad eating habits, disorders in nutrient absorption, or increased nutrient demands. A minority of patients suffer from metabolic disorders in the transsulfuration pathway;

some enzymes have low activity or do not function at all. Thus there is a need for a nutritional product which supports total methionine metabolism and at the same time compensates for the shortages in nutrients that may occur in patients in need of support of methionine metabolism.

Several intermediates of total methionine metabolism can be quite reactive in the human body, and the reactive forms (reduced homocysteine, cysteine, glutathione) are not easily transported over the cell membranes. It is therefore important to support the methionine metabolism in such a way that no undesired side effects occur and at the same time intracellular levels of useful intermediates are maintained, even in the diseased state.

The reactive species are also easily oxidised in aqueous solution, and it is therefore an object of the invention to provide a nutritional composition with a sufficient shelf stability. Some nutritional components that play an important part in the methionine metabolism have bad organoleptic properties. It is therefore an object of the invention to provide a nutritional product that is well acceptable to the consumer.

Many attempts have been made up to now to find solutions to these problems. All these prior attempts have concentrated on a part of the total methionine metabolism, relying on an adequate functioning of the rest of the biochemical pathways of total methionine metabolism in man to maintain homeostasis and meet physiological demands. For supporting these parts, either too low or too high amounts were suggested.

It has now been found that it is essential to provide patients with a combination of components that play a key role in the various parts of total methionine metabolism as depicted in the scheme below, and to provide them in an excess amount in the form of a (medicated) nutritional composition in order to give nutritional support to the maximum number of patients. In this context "nutritional" means at least partly satisfying the energy needs in addition to having a medicinal effect.

It has furthermore been found to be advantageous to administer other components that play a role in total methionine metabolism as well. Such other components comprise end products and intermediates for giving a more rapid response and for meeting requirements for those patients that have deficiencies in one or more key enzymes that are involved in total methionine metabolism.

The invention pertains to an enteral food composition containing at least digestible, in particular glucose or α-glucan, carbohydrates and proteins or protein hydrolysates and a combination of active components as defined in the appending claims. The amounts of the components of the food composition of the invention are related to the Recommended Daily Allowance (RDA) and other recommendations as used in standard nutrition literature. The reference values based on these RDA values for components that can be used according to the invention, together with the preferred ranges of total intake per day, are given in table 1 below. The reference are based on healthy adults having a body weight of 70 kg. For patients of different condition and different body weight, the levels should be adapted accordingly. It is to be understood that on average the energy intake per day should be about 2000 kcal.

Where reference is made to nutritional equivalents of the components, this includes any compound which under physiological conditions yields the component in question in equimolar amounts.

TABLE 1

Reference values and preferred levels according to the invention

| component | reference mg/day | general mg/day | preferred mg/day |
|---|---|---|---|
| methionine/cysteine* | 1100 | 600–7,000 | 1,600–4,000 |
| folic acid | 0.2 | 0.4–8 | 0.6–3 |
| pyridoxal | 2.0 | 3.2–20 | 4–12 |
| cyanocobalamine | 0.0015 | 0.002–0.02 | 0.0036–0.01 |
| magnesium | 300 | 200–700 | 300–500 |
| riboflavin | 1.5 | 2–10 | 2.5–6 |
| niacin | 17 NE | 25–170 | 35–85 |
| thiamine | 1.5 | 2–10 | 3–6 |
| zinc | 12 | 24–120 | 24–100 |
| manganese | 6 | 9–60 | 10–30 |
| copper | 2.0 | 3–14 | 4–10 |
| selenium | 0.07 | 0.08–0.3 | 0.1–0.15 |
| ascorbic acid | 65 | 100–900 | 150–300 |
| tocopherol | 10 a-TE | 15–180 | 20–40 |

*as methionine, S-adenosyl methionine, S-adenosyl homocysteine, homocysteine, cystathionine, cysteine, cystine, glutathione or other equivalents (see text).

Nutritional equivalents of amino acids include di- or oligopeptides incorporating said amino acid, esters, amides and salts of the amino acids, as well as S-substituted derivatives in the case of sulphur-containing amino acids, including methionine, S-acetylmethionine, S-acetylhomocysteine, homocysteine, cystathionine, cysteine, cystine, glutathione and other dimers and trimers derived from these. The sulphur amino acids other than methionine and cysteine can be used instead as a substitute of methionine and cysteine, although the latter two are preferred. Suitable examples of a cysteine equivalent are N-acetylcysteine and bisglycylcystine. Proteins may also be used as amino acid sources, provided that the desired amino acids become readily available by digestion. Methionine-rich proteins include e.g. casein, caseinates and casein hydrolysates. Cysteine-rich proteins include dairy whey proteins and specific proteins thereof such as lactalbumin, as well as blood proteins, egg proteins and other proteins which are rich in sulphur-containing amino acids and hydrolysates thereof. Thus the required level of sulphur-containing amino acids can be attained e.g. by combining casein with cysteine, N-acetylcysteine or a cysteine-rich peptide or by combining whey protein with methionine or a methionine-rich peptide. Preferably, proteins that are rich in essential amino acids are also present.

Nutritional equivalents of pyridoxal (vitamin $B_6$) include pyridoxal phosphate, pyridoxine and pyridoxamine and salts and the like. Nutritional equivalents of niacin (nicotinic acid) include niacinamide (nicotinamide) and tryptophan. The preferred equivalent of thiamine (vitamin $B_1$) is its hydrochloride.

Among the components given in table 1, methionine/cysteine, folic acid, pyridoxal and zinc should be present in addition to the energy content. These components, including the carbohydrate content, were found to be essential as primary support of the transsulfuration pathway. At least half of the methionine/cysteine content should consist of methionine or a methionine equivalent. A second group of important components includes magnesium, cyanocobalamine and betaine/choline. Preferably, at least one of these is also present in the food compositions of the invention. Magnesium is preferred, but at around or slightly above the reference level only. Suitable magnesium salts include magnesium hydrogen phosphate and magnesium sulphate. A third group comprises transsulfuration products, including creatine, carnitine, taurine and nucleotides. At least one of these is also advantageously present in the food composition. A fourth group of components is important as they stimulate carbohydrate metabolism and produce ATP and reducing equivalents. At least one member of this group which includes pyruvate, thiamine, riboflavin, niacin, biotin and thioctic acid, is preferably present as well. A final group comprises ascorbic acid, tocopherol, selenium, copper and manganese. The incorporation of ascorbic acid and/or tocopherols is preferred for ensuring that reduced glutathione is spared from excessive attack by radicals or oxidation processes. Ascorbic acid may be present as a nutritionally acceptable salt, and tocopherol as any one or a combination of isomers, e.g. tocopherol. Other antioxidants or radical scavengers like carotenoids, flavonoids, uric acid etc. may be included as well. Similarly, the trace elements Cu, Se and Mn are preferably included, as they are essential for key enzymes that neutralise oxygen-containing radicals. The preferred range for Cu and Mn is 2–5 times the reference value; for selenium it is about 1.5 times the reference value.

The other components of table 1 are also preferred individually, i.e. the selection of a single component, e.g. riboflavin or manganese, forms a distinct embodiment of the invention. Components for which a reference level is not given in table 1, are also advantageously incorporated in the composition of the invention. The methyl donor betaine (N,N,N-trimethylglycine, as its inner salt or its hydrochloride) and/or one of its precursors choline and phosphatidylcholines (occurring in certain lecithins) is preferably included in order to stimulate an independent pathway for the conversion of homocysteine to methionine. For reasons of taste, betaine itself is preferred over its equivalents.

Creatine (N-guanidyl-N-methylglycine) can be incorporated as such, as its phosphate or as an analogue such as guanidine derivatives, in the levels indicated, with a preferred level of around 10 g/day. L-Carnitine can be given as such (inner salt) or as its hydrochloride. Creatine and/or carnitine are especially preferred for patients having a poor blood circulation, or suffering from local ischaemic conditions. D-Biotin (generally preferred) and taurine can be included as such, taurine especially for infants and neurological patients. Nucleotides can also be advantageously included, preferably as yeast extract in an amount of about 0.1–4 g/day, for example in products for the treatment of inflammatory diseases of the gut.

Pyruvate is another component that can contribute to the ATP production and can protect glutathione as a radical scavenger. The preferred level is from 2 to 20 g/day, especially 4–8 g/day. Pyruvate can be incorporated e.g. as free acid or as its Ca, Na or K salt. DL-Thioctic acid (lipoic acid) is also preferred for increasing the level of ATP produced. Niacin, riboflavin and thiamine also stimulate carbohydrate metabolism and produce ATP and reducing equivalents.

Furthermore, usual components can be incorporated at or above the recommended amounts, especially calciferol/cholecalciferol/dihydrocalciferol (vitamin D) and phosphate. The composition should comprise sufficient levels of essential amino acids such as lysine in accessible form, so that the total intake corresponds at least to the reference levels. Some non-essential amino acids are also preferably included in the composition of the invention. These comprise especially serine, and furthermore glutamine and arginine/ornithine at the indicated levels as such (L-form) or as easily degradable peptides or proteins. Threonine is preferably not present in important amounts, i.e. preferably lower than 5.2 g per 6.25 g of nitrogen (<5.2 g per 100 g of proteinaceous material). Proteins which are low in threonine include acid whey.

The compositions contain carbohydrates, preferably proteins and preferably fats. In a complete food, the carbohydrates should constitute at least 25% of the required energy content, i.e. at least 400 kcal/day, up to 1500 kcal/day. The carbohydrates can comprise mono-, di-, oligo- and polysaccharides, such as glucose, fructose, maltose, sucrose, fructo-, galacto- and especially gluco-oligosaccharides, starch, starch hydrolysates and starch fractions and the like. The carbohydrate composition can be adapted to the type of patients. For diabetes patients, slowly degrading carbohydrates like fructose polymers may be present together with a relatively large amount of high molecular weight maltodextrins. Generally, the carbohydrate compositions is low in lactose. The compositions may furthermore contain dietary fibres such a non-digestible carbohydrates. The proteins may be those described above as sources for the desired amino acids, including milk proteins, egg proteins, blood proteins. For reasons of taste, it is preferred that at least half of the total proteinaceous material (proteins, hydrolysates and amino acids) is in the form of proteins or peptides, especially in the form of intact proteins.

The fats may comprise normal fats $C_{12}$–$C_{18}$ derived from saturated and especially unsaturated fatty acids. The fats may include medium chain triglycerides derived from $C_8$ and $C_{10}$ fatty acids (e.g. accounting for 5–40 wt. % of the fats), and preferably polyunsaturated long-chain ($\geq C_{18}$) fats (PUFA's) derived from ω-3 fatty acids such as eicosapentaenoic acid (EPA) and docosahexaenoic acid (DHA) (preferably at least 3 wt. %, in particular 5–15 wt. % of the fats). The ω-3/ω-6 ratio is preferably from 0.3 to 3. For complete foods, the fat content is preferably more than 30% of the total energy content, especially more than 35 en. %, up to 45 en. %. The fats should contain phospholipids such as lecithin or an equivalent thereof at a level of 1–20 wt. % of the fat content, or 0.3–10 en. %, preferably 0.6–5 en. % of the composition. The phospholipids can be partly (i.e. the amount above 5 wt. % of the fat content) substituted by equivalents such as choline or betaine.

The food composition can have the form of a complete food, i.e. all the nutritional needs of the user. As such it will usually containing 1200–2500 kcal per daily dosage, apart from higher or lower amounts in exceptional cases. The daily dosage amounts are given with respect to a daily energy supply of 2000 kcal, but can be adapted accordingly. The complete food can be liquid, wherein the daily dosage is contained in e.g. 2000 ml; more diluted or, especially, more concentrated liquids can also be used. The composition can also be in solid form for reconstitution with water. The complete food can be in the form of multiple dosage units, e.g. from 3 to 10 per day.

The food composition of the invention can also be a food supplement to be used in addition to a non-medicinal food, containing less than 1500 kcal, in particular 400–1000 kcal, per daily dosage. Such food supplement preferably also contains at least part of the carbohydrate and protein supply, so that the need of essential amino acids and serine is met with the supplement. A very useful supplement contains the essential components at the levels indicated above (methionine/cysteine, folic acid, vitamin $B_6$, zinc and optionally magnesium, vitamin $B_{12}$, betaine/choline, serine and/or tryptophan with a suitable carrier such as maltodextrin in dry form, e.g. in sachets of 10 g. The content of the sachet may be added to regular food or to food components so as to provide the daily doses according to the invention.

The invention also relates to a process of producing a food composition, which comprises preparing a premix of at least said methionine/cysteine, folic acid, pyridoxal and zinc, optionally with a relatively small amount of maltodextrin or other carbohydrate as a carrier. Further components are then added to said premix, for example by subsequent addition of other premixes. The use of premixes may simplify and/or standardise the preparation of especially adapted food compositions directed at specific needs. Also from an economical point of view, and from the point of view of minimising mistakes during processing, it is therefore advantageous to produce a single premix of components that can be used in the manufacture of several types of enteral clinical nutrition.

As the module of components supports total methionine metabolism, it has universal benefit in many types of clinical nutrition. The universal character of the food composition of the invention obviates the need to await the result of some types of clinical analyses of patients. The module can be added in response to specific nutritional demands. The compositions can be adapted for clinical nutrition, infant formulae, nutrition for persons at risk for specific diseases, enteral nutrition during pregnancy, and dietetic supplements. The food compositions can be used for the treatment or prophylaxis of increased plasma level of homocysteine, cardiovascular diseases, imparted immune function, inflammatory diseases, autoimmune diseases such as arthritis, wound healing after surgery, decubitus, cancer, premature ageing, allergic conditions, neural disorders,

EXAMPLE 1

Three standard mixtures of active components were prepared by dry mixing the amounts as indicated in tables 2 and 3 and optionally table 4.

TABLE 2

Ingredient mixture A for support of total methionine metabolism

| | amount per 100 kg of premix A |
|---|---|
| maltodextrins | 74 kg |
| L-methionine | 8 kg |
| N-acetylcysteine | 2 kg |
| folic acid | 6 g |
| pyridoxine | 60 g |
| zinc sulphate | 500 g (=200 g Zn) |
| cyanocobalamine on carrier | 30 g (=30 mg B12) |
| magnesium phosphate 3 aq. | 14 kg (=2 kg Mg) |

TABLE 3

Ingredient mixture B for support of total methionine metabolism

| | amount per 100 kg of premix B |
|---|---|
| maltodextrins | 89 kg |
| betaine | 10 kg |
| nicotinamide | 510 g NE |
| riboflavine | 30 g |
| thiamine.HCl | 30 g |
| manganese sulphate 4 aq. | 320 g (=80 g Mn) |
| cupric sulphate 5 aq. | 150 g (=40 g Cu) |

TABLE 4

Ingredient mixture C for support of total methionine metabolism

| | amount per 200 kg of premix C |
|---|---|
| maltodextrins | 40 kg |
| creatine | 100 kg |
| L-carnitine | 12 kg |
| taurine | 400 g |
| ascorbic acid | 2.0 kg |
| alfa-tocopherol | 200 g TE |
| soy lecithin | 5 kg |
| L-biotin on a carrier | 200 g (=2 g L-biotine) |
| sodium selenate on a carrier | 370 g (=1 g Se) |
| L-serine | 30 kg |
| L-tryptophan | 10 kg |

EXAMPLE 2

Complete Enteral Tube Feeding in Dry Form.

The ingredients as listed below are dissolved in 2000 l water.

Composition of aqueous phase of complete enteral nutrition

| | amount per 2000 l |
|---|---|
| caseinates (50% Na, 50% Ca) | 60 kg |
| protein isolate from acid whey | 40 kg |
| ingredient mixture A | 10 kg |
| ingredient mixture B | 10 kg |
| ingredient mixture C | 20 kg |
| maltodextrins | 280 kg |
| L-arginine | 6 kg |
| wheat hydrolysate | 30 kg |
| fibres (inulin/soy: 2/1) | 16 kg |
| calcium phosphate | 0.6 kg |
| magnesium phosphate | 0.4 kg |
| sodium chloride | 0.9 kg |
| potassium citrate | 5 kg |
| lecithin | 4.4 kg |
| standard trace element premix (which comprises 20 g Fe, 3 g Cu, 100 mg Mo, 2 mg F, 20 g Zn, 6 g Mn, 66 mg Cr, 200 mg I, 40 mg Co and 10 g Se) | 250 g |
| standard vitamin premix (which comprises pantothenic acid 8 g, thiamine 2 g, riboflavin 2.2 g, niacin 4.2 g NE, vitamin B6 2.6 g, biotine 200 mg and folic acid 260 mg) | 20 g |
| meso-inositol | 50 g |
| yeast extract | 1 kg |

After dissolving the ingredients, the aqueous phase is set on pH 6.5–8 and stirred until use. In a separate tank the fat blend as exemplified below is prepared by methods known in the art (pumping the appropriate amounts in the tank at elevated temperature (e.g. 50° C.) and the fat-soluble vitamins (A, D2, K and E) are added and the mixture stirred until use).

| Fat blend composition; amounts in kg per 100 kg | |
|---|---|
| sunflower oil (high oleic acid) | 28 |
| sunflower oil | 12 |
| rapeseed oil | 52 |
| fish oil (high DHA) | 2 |
| MCT oil | 6 |
| vitamin premix | |
| vitamin A | 1.4 g |
| vitamin D2 | 10 mg |

-continued

| Fat blend composition; amounts in kg per 100 kg | |
|---|---|
| vitamin K | 100 mg |
| vitamin E | 100 g |

The aqueous phase is pumped to a homogeniser arranged before a pasteuriser and static mixer. The fat phase is carefully dosed to the aqueous phase before it reaches the mixer, in a ratio of 1 part fat phase to 16 parts of the pasteurised aqueous phase. Immediately thereafter the mixture is homogenised and pumped to a heat exchanger where the water is evaporated and the resulting product spray-dried and packed in cans.

EXAMPLE 3

A Nutritional Supplement for the Elderly

In 2000 liter tap water are dissolved:

| | |
|---|---|
| 70 kg | skimmed milk powder (delactosed) |
| 64 kg | saccharose |
| 5 kg | soy lecithin |
| 10 kg | algae oil |
| 10 kg | canola oil |

This mixture is pasteurised and fermented.
Then are added:

| | |
|---|---|
| 20 kg | mixture A (of example 1) |
| 6 kg | pectine |
| 200 kg | glucose syrup (Glucidex) |
| 2 kg | choline chloride |
| 2.4 kg | calcium chloride |
| 2.4 kg | potassium phosphate |
| 1.5 kg | potassium lactate |
| 260 g | sodium ascorbate |
| 2.0 kg | potassium citrate |
| 40 kg | fruit concentrate |
| 1 kg | flavourings |

The mixture is set on pH 3.8–4.4, pasteurised and filled aseptically into 500 ml cartons.

EXAMPLE 4

Supplement for Persons qith Volume Restrictions (Infants, Persons Suffering from Illness, Cancer or Neuropathic Diseases)

Packed in 1 liter cartons.

| | Amount per 100 ml |
|---|---|
| Energy | 150 kcal |
| Protein (casein/whey 80/20) | 8.2 g (=0.3 g Met + Cys) |
| Tryptophan | 0.1 g |
| Carbohydrates | 16.5 g |
| Maltodextrin | 10.5 g |
| Sucrose | 6.0 g |
| Fats | 5.5 g |
| Saturated | 1.3 g |
| Mono-unsaturated | 1.8 g |
| PUFA's | 2.1 g |
| from vegetable oils, lecithin + DHA/EPA source (0.1 g) | |
| Fibre (inulin/soy 1:1) | 0.4 g |
| Sodium | 60–100 mg |
| Potassium | 140–210 mg |
| Chloride | 80–150 mg |
| Calcium | 230 mg |
| Phosphorus | 150 mg |
| Magnesium | 35 mg |
| Iron | 2.0 mg |
| Zinc | 6.0 mg |
| Copper | 0.6 mg |
| Manganese | 2.0 mg |
| Fluorine | 0.2 mg |
| Molybdene | 10 µg |
| Selenium | 10 µg |
| Chromium | 6.6 µg |
| Iodine | 20 µg |
| Vitamin A | 166 µg RE |
| Vitamin D | 2.0 µg |
| α-Tocopherol | 4.9 mg |
| Vitamin K | 8.0 µg |
| Thiamine | 0.4 mg |
| Riboflavin | 0.4 mg |
| Niacin | 6 mg NE |
| Pantothenic acid | 0.8 mg |
| Vitamin $B_6$ | 1.0 mg |
| Folic acid | 100 µg |
| Vitamin $B_{12}$ | 0.3 µg |
| Biotin | 20 µg |
| Vitamin C | 13 mg |
| Betaine | 20 mg |
| Taurine | 4 mg |

EXAMPLE 5

Food Supplement

The mixture of table 2 (example 1) was filled in sachets of 10 g each.

Scheme of methionine metabolism (Met = methionine, Hcy = homocysteine, GSH = reduced glutathione, GSSG = oxidised glutathione)

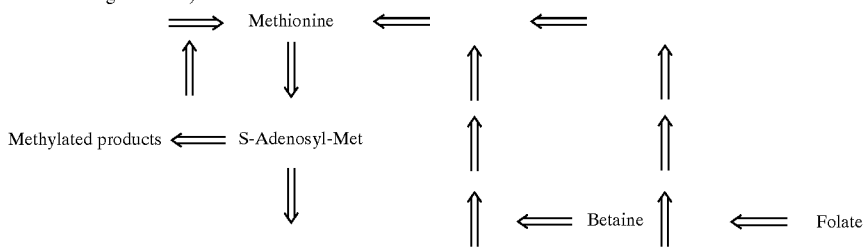

-continued

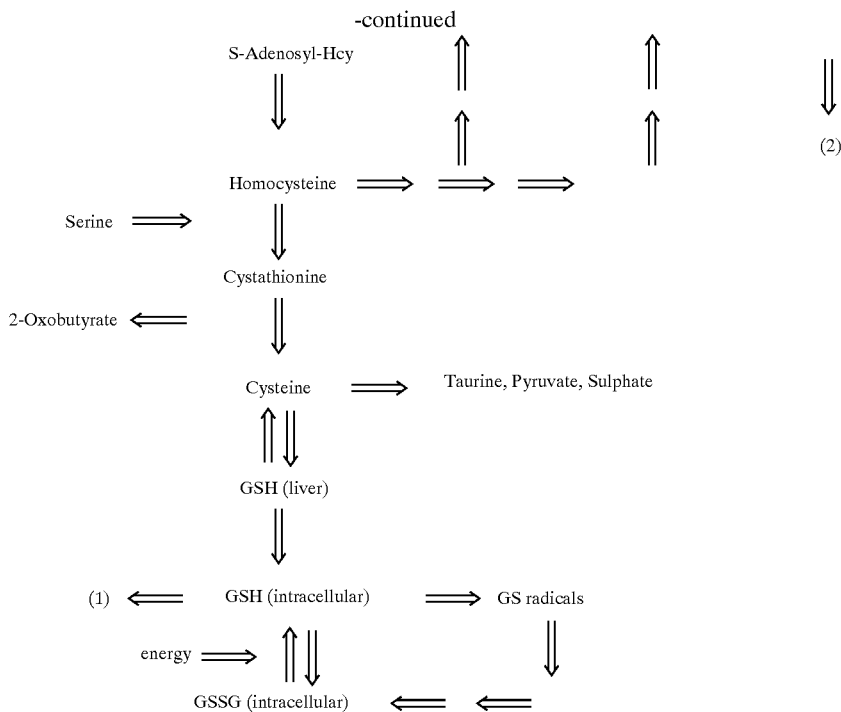

(1) Cofactor function, Amino acid Transport and Detoxification
(2) Pyrimidine metabolism, One-carbon Pool and Gly/Ser metabolism

What is claimed is:

1. Food composition which is a complete enteral food for clinical or dietary use, containing per daily dosage:
   (a) an energy content of 1200–2500 kcal, supplied by carbohydrates, fats and proteinaceous material, the carbohydrates accounting for at least 25% of the energy content, the fats accounting for 35–45% of the energy content and the proteinaceous material being present in an amount of at least 20 g, at least 50% of the proteinaceous material being present as proteins or peptides, and
   (b) the following components: 0.6–7 g of methionine and cysteine taken together, 0.4–8 mg of folic acid, 3.2–20 mg of pyridoxal and 24–120 mg of zinc;
   (c) at least one component selected from cyanocobalamine, magnesium and betaine and/or choline;
   (d) at least one component selected from creatine, carnitine, taurine, and nucleotides; and
   (e) at least one component selected from pyruvate, riboflavin, niacin, thiamine, D-biotin, and thioctic acid.

2. Food composition according to claim 1, further comprising, per daily dosage:
   (c) at least one component selected from cyanocobalamine 2–20 μg, magnesium 200–700 mg and betaine and/or choline 0.3–6 g;
   (d) at least one component selected from creatine 0.5–40 g, carnitine 0.2–4 g, taurine 15–150 mg, and nucleotides 0.1–4 g; and
   (e) at least one component selected from pyruvate 2–20 g, riboflavin 2–10 mg, niacin 25–170 mg, thiamine 2–10 mg, D-biotin 50–500 μg, and thioctic acid 5–200 mg;
   (f) at least one of the following components: manganese 9–60 mg, copper 3–14 mg, selenium 80–300 μg, ascorbic acid 100–900 mg, and tocopherol 15–180 mg; and
   (g) at least one of the following components: serine 3–12 g, glutamine 5–30 g, the composition containing less than 5.2 g of threonine per 100 g of proteinaceous material.

3. Food composition which is an enteral food supplement for clinical or dietary use to be used in addition to a non-medicinal food, containing per daily dosage:
   (a) an energy content from 400 to less than about 1500 kcal, supplied by at least carbohydrates and proteinaceous material, soluble digestible carbohydrates being present in amount of at least 100 g and the proteinaceous material being present in amount of at least 20 g, at least 50% of the proteinaceous material being present as proteins or peptides, and
   (b) the following components: 0.6–7 g of methionine and cysteine, 0.4–8 mg of folic acid, 3.2–20 mg of pyridoxal and 24–120 mg of zinc;
   (c) at least one component selected from betaine, choline and phospholipids, and at least one component selected from cyanocobalamine, magnesium and betaine and/or choline;
   (d) at least one component selected from creatine, carnitine, taurine, and nucleotides; and
   (e) at least one component selected from pyruvate, riboflavin, niacin, thiamine, D-biotin, and thioctic acid.

4. Food composition according to claim 3, containing 400–1000 kcal per daily dosage.

5. Food composition according to claim 3, further comprising, per daily dosage:
   (c) at least one component selected from cyanocobalamine 2–20 μg, magnesium 200–700 mg and betaine and/or choline 0.3–6 g;
   (d) at least one component selected from creatine 0.5–40 g, carnitine 0.2–4 g, taurine 15–150 mg, and nucleotides 0.1–4 g; and (e) at least one component selected from pyruvate 2–20 g, riboflavin 2–10 mg, niacin 25–170 mg, thiamine 2–10 mg, D-biotin 50–500 µg, and thioctic acid 5–200 mg;

(f) at least one of the following components: manganese 9–60 mg, copper 3–14 mg, selenium 80–300 µg, ascorbic acid 100–900 mg, and tocopherol 15–180 mg; and (g) at least one of the following components: serine 3–12 g, glutamine 5–30 g, the composition containing less than 5.2 g of threonine per 100 g of proteinaceous material.

6. Food composition according to claim 3, further comprising at least one of the following components, per daily dosage:

(c) cyanocobalamine 3.6–10 µg, magnesium 300–500 mg and betaine and/or choline 0.6–3 g;

(d) creatine 2–25 g, carnitine 0.4–2 g, taurine 30–80 mg, and nucleotides 0.4–2 g (e) pyruvate 4–8 g, riboflavin 2.5–6 mg, niacin 35–85 mg, thiamine 3–6 mg, D-biotin 100–300 µg, and thioctic acid 10–50 mg;

(f) manganese 10–30 mg, copper 4–10 mg, selenium 100–150 µg, ascorbic acid 150–300 mg, and tocopherol 20–40 mg;

(g) serine 3–12 g and optionally arginine or ornithine 2–10 g, glutamine 5–30 g, the composition containing less than 5.2 g of threonine per 100 g of proteinaceous material.

7. Food composition according to claim 3, which is in a liquid form having an energy density of at least 1–2.5 kcal/ml.

8. Food composition according to claim 3, which is in a powder form to be reconstituted with water.

9. A process for the treatment of impaired methionine metabolism in humans, comprising administering to a human suffering from impaired methionine metabolism, an effective amount of the following composition per daily dosage:

(a) an energy content from 400 to less than about 1500 kcal, supplied by at least carbohydrates and proteinaceous material, soluble digestible carbohydrates being present in amount of at least 100 g and the proteinaceous material being present in amount of at least 20 g, at least 50% of the proteinaceous material being present as proteins or peptides, and (b) the following components: 0.6–7 g of methionine and cysteine, 0.4–8 mg of folic acid, 3.2–20 mg of pyridoxal and 24–120 mg of zinc;

(c) at least one component selected from cyanocobalamine, magnesium and betaine and/or choline;

(d) at least one component selected from creatine, carnitine, taurine, and nucleotides; and (e) at least one component selected from pyruvate, riboflavin, niacin, thiamine, D-biotin, and thioctic acid.

10. The food composition according to claim 1, wherein 1–20% of the fat content is provided as phospholipids.

* * * * *